United States Patent [19]

Haruna et al.

[11] Patent Number: 4,885,326

[45] Date of Patent: Dec. 5, 1989

[54] COMPOSITION OF STABILIZED SYNTHETIC RESIN

[75] Inventors: Tohru Haruna, Okegawa; Kazunori Nishikawa, Matsudo; Mitsuhiro Hamajima, Kashiwa, all of Japan

[73] Assignee: Adeka Argus Chemical Co., Ltd., Tokyo, Japan

[21] Appl. No.: 328,313

[22] Filed: Mar. 24, 1989

[30] Foreign Application Priority Data

Apr. 2, 1988 [JP] Japan .................................. 62-81866

[51] Int. Cl.$^4$ ............................................. C08K 5/52
[52] U.S. Cl. .................................... 524/291; 524/101; 524/108; 524/117
[58] Field of Search ................. 524/291, 101, 108, 117

[56] References Cited

U.S. PATENT DOCUMENTS

| | | | |
|---|---|---|---|
| 3,297,631 | 1/1967 | Bown et al. | 524/117 |
| 4,252,750 | 2/1981 | Buysch et al. | 524/117 |
| 4,351,759 | 9/1982 | Spivack | 524/117 |

FOREIGN PATENT DOCUMENTS

| | | |
|---|---|---|
| 0023291 | 2/1981 | European Pat. Off. |
| 429070 | 5/1974 | U.S.S.R. |
| 440390 | 8/1974 | U.S.S.R. |

*Primary Examiner*—Veronica P. Hoke
*Attorney, Agent, or Firm*—Barnes, Kisselle, Raisch, Choate, Whittemore & Hulbert

[57] ABSTRACT

A synthetic resin composition comprises 100 parts by weight of a synthetic resin, 0.001 to 10 parts by weight of a cyclic alkylphosphite compound of 2,2'-alkylidene-bisphenol (I) and 0.001 to 10 parts by weight of beta-(3,5-dialkyl-4-hydroxyphenyl)-propionic acid ester (II) and is stabilized to light and heat.

1 Claim, No Drawings

COMPOSITION OF STABILIZED SYNTHETIC RESIN

The present invention relates to compositions of stabilized synthetic resins and more specifically to those compositions of synthetic resins which are made more stable and resistant to deterioration by heat and light, by adding particular cyclic phosphonite compounds and particular phenol ester antioxidants.

It is well known that polyethylene, polypropylene, ABS resins, polyvinyl chloride resins and other similar synthetic resins are deteriorated, colored or lowered in their mechanical strength by the action of heat and light, thus becoming less endurable to a long-term use.

In order to prevent such deterioration, a plenty of additives have so far been used either independently or in combination. It is also known that among these additives, the phosphonite compounds are of relatively great effectiveness in improving the heat resistance and controlling the coloration. As these phosphite compounds generally are used trialkyl phosphite, triallyl phosphite, alkyl-allyl phosphite and other triorganic phosphiate compounds or acidophosphiate compounds having a hydroxyl group instead of an organic group.

These phosphiates however still remain insufficient not only in their stabilizing effect but also in water resistance.

Out of the organic phosphiate compounds, such cyclic phosphiate compounds as bisphenols are relatively excellent in stabilizing effect and water resistance. For example, U.S. Pat. No. 3,297,631 proposes 2,2'-methylenebis (dialkylphenyl) phosphite compounds, but the stabilizing effect of this compound still remains virtually insufficient and does not meet the practical use. Though Japanese Provisional Patent Publication No. 100391-1979 proposes, as an improved phosphite compound, a cyclic phosphite compound of orthobiphenol and Japanese Provisional Patent Publications No. 114595-1982 and No. 103-537-1983 cyclic phosphite compounds of 2,2'-bisphenols respectively, their effectiveness remains yet insufficient. They are not practical due also to the complication of their manufacturing method.

Phenol based antioxidants are generally used as base antioxidants for a wide variety of synthetic resins and so far a great number of compounds are known: mononuclear phenols such as 2,6-ditributyl-4-methyl phenols, polynuclear phenols such as alkylidenebis or trisphenols, esters such as 3,5-ditributyl-4-hydroxyphenyl propionic acid.

Further, it is known that synergism can be had by combined use of these phenol antioxidants and varied phosphite compounds, but the effect of conventional combinations is practically not satisfying that is, insufficient, for example, in stability, long-term heat resistance and coloration by radiation of heat.

As a result of our researches to eliminte the disadvantaages as above and to remarkably improve the processing stability, heat resistance and light resistance and so forth, we eventually found that by combined addition of the cyclic alkylphosphite compounds of 2,2'-alkylidenebis phenol and β-(3,5-dialkyl-4-hydroxyphenyl) propionic acid ester compounds to accomplish the present invention.

The present invention provides a composition of stabilized synthetic resin resulting from 100 parts of synthetic resin to which area dded 0.001 to 10 parts in weight of a compound represented by the general formula (I) and 0.001 to 10 parts in weight of another compound represented by the general formula (II) below:

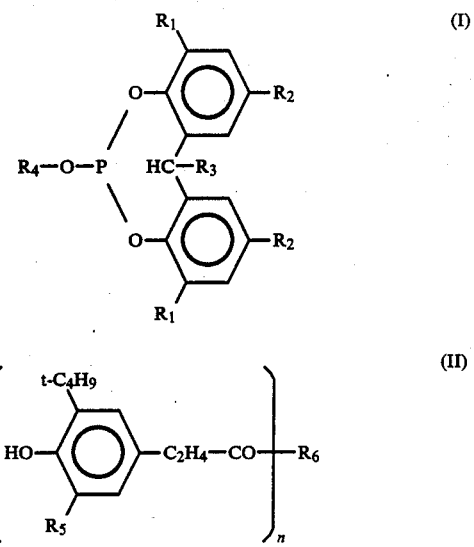

in which R1 is tertiary-butyl (t-butyl) or tertiary-amyl (t-amyl), R2 is an alkyl having 1 to 9 carbon atoms, R3 is hydrogen or an alkyl having 1 to 4 carbon atoms, R4 is an alkyl having 1 to 30 carbon atoms, R5 is an alkyl having 1 to 4 carbon atoms, R6 is a residual group of a monohydric alcohol, a dihydric alcohol, a trihydric alcohol or a tetrahydric alcohol from which its hydrogen is removed and n is a number of 1 to 4.

In the above formulas (I) and (II), we can enumerate, as the alkyl group with 1 to 9 carbon valency represented by R2, methyl, ethyl, propyl, isopropyl, butyl, secondary butyl, tertiary butyl, isobutyl, amyl, tertiary amyl, hexyl, heptyl, octyl, isooctyl, 2-ethylhexyl, tertiary octyl, nonyl, tertiary nonyl and so forth. As the alkyl group with 1 to 4 carbon atomicity to be represented by R3 and R5, we enumerate methyl, ethyl, propyl, isopropyl, butyl, secondary butyl, tertiary butyl, isobutyl; and as the alkyl group with 1 to 30 carbon atomicity represented by R4: methyl, ethyl, propyl, isopropyl, butyl, secondary butyl, tertiary butyl, isobutyl, amyl, tertiary amyl, hexyl, heptyl, octyl, isooctyl, 2-ethylhexyl, tertiary octyl, nonyl, tertiary nonyl, decyl, isodecyl, dodecyl, tetradecyl, hexadecyl, octadecyl, eicosyl, docosyl, tetracosyl, tracontyl and so forth.

As monohydroxy to tetrahydroxy alcohol giving the residual group R6, there are methanol, ethanol, butanol, octanol, 2-ethylhexanol, isooctanol, decanol, dodecanol, tetradecanol, hexadecanol, octadecanol and other monohydroxy alcohol; ethylene glycol, propylene glycol, 1,4-butanediol, 1,6-hexanediol, 1,10-decanediol, diethylene glycol, dipropylene glycol triethylene glycol, thiodiethylene glycol, 3,9-bis (2-hydroxy-1,1-dimethylethyl)-2,4,8,10-tetraoxaspiro((5,5))undecane, 2,2-bis(4-(2-hydroxyethoxyphenyl)propane and other dihydric alcohols; glycerin, trimethylolethane, trimethylolrpoane, tris(2-hydroxyethyl) isocyanurate and other trihydric alcohols; pentaerythritol, diglycerin, ditrimethylolpropane and other tetra hydric alcohols.

Such typical phosphite compounds as represented by the above general formula (I) which are used in the present invention are the followings:
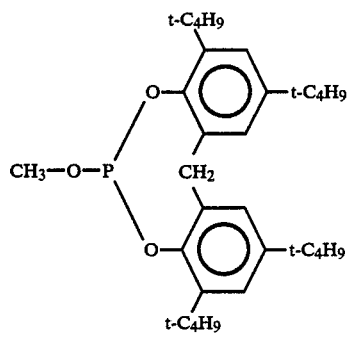
I-1
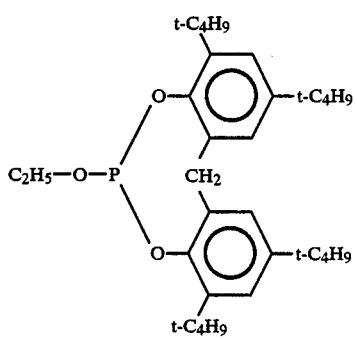
I-2
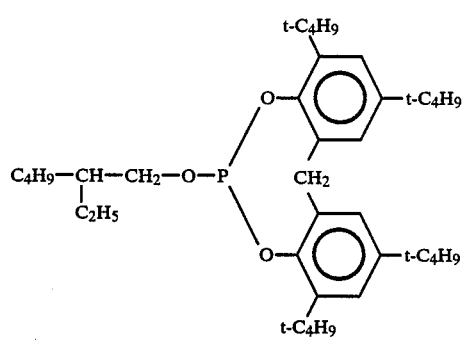
I-3
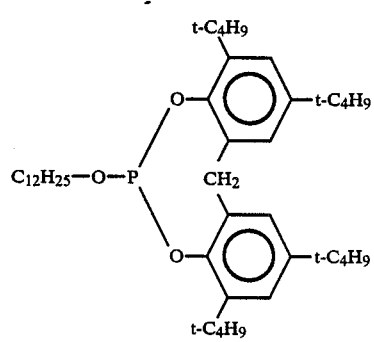
I-4
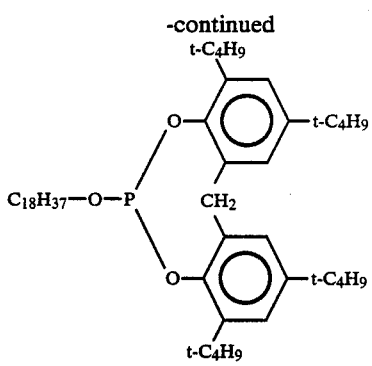
I-5
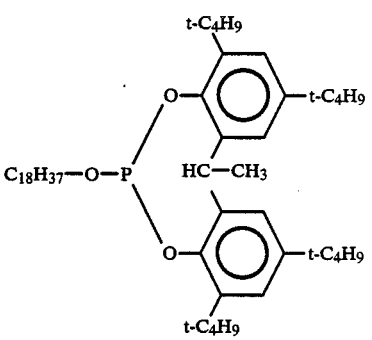
I-6
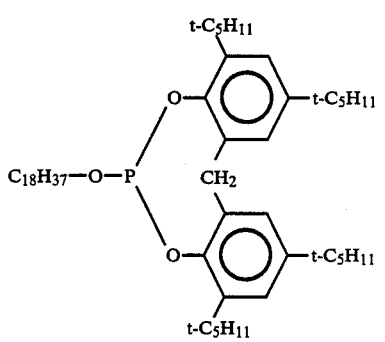
I-7
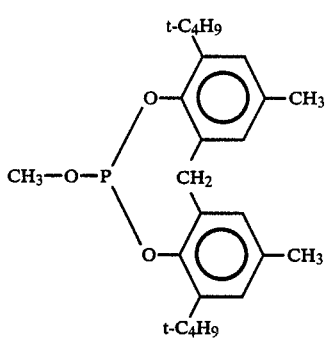
I-8
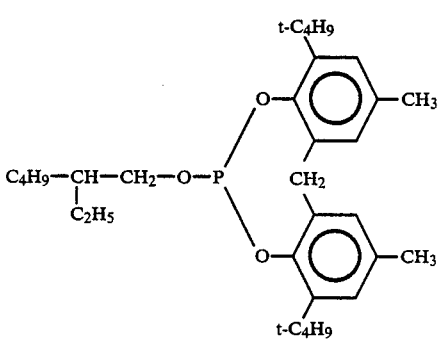
I-9

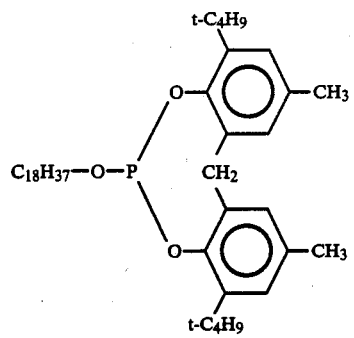

I-10

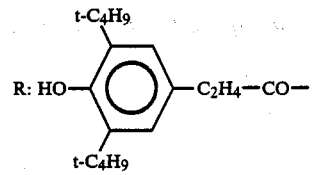

R:

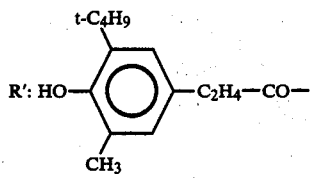

R':

R—O—C₁₈H₃₇  II-1

R'—O—C₁₈H₃₇  II-2

R—O—C₆H₁₂—O—R  II-3

R'—O(C₂H₄O)₃—R'  II-4

R—O—C₂H₄—S—C₂H₄—O—R  II-5

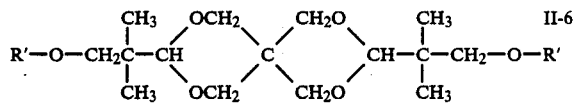

II-6

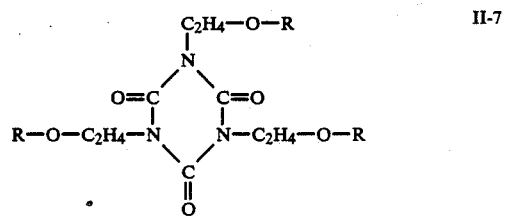

II-7

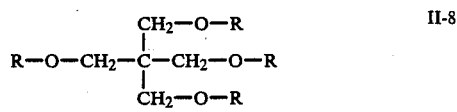

II-8

The compound represented by the formula (I) can be obtained by allowing, for example, phosphorous trichloride to react with 2,2'-alkylidenebisphenol into a compound in which $R_4$—O— as in this formula be chlorine atom, which will then be allowed to react with an alcohol to be represented by $R_4$—OH.

The present invention will be understood more easily with reference to the following examples of syntheses of the above compound; however these examples are intended to illustrate the invention and are not to be construed to limit the scope of the invention.

EXAMPLE OF SYNTHESIS 2,2'-methylenebis (4,6-dit- butylphenyl)stearylphophite (Compound I-5)

Into a 500 ml four-neck flask, 42.5 g of 2,2'-methylenebis (4,6-ditributylphenol), 100 g of toluene and 0.86 g of triethylamine were put. Stirring this mixture 16.5 g of phosphorous trichloride was dropped into at 60° to 65° C. After this dropping the temperature of the mixture was gradually raised in a stream of nitrogen, then stirred under reflux for 2 hours.

Excessive phosphorous trichloride was distilled off under reduced pressure. After cooling down to 60° C., 12.1 g of triethylamine and 27 g of stearyl alcohol were added and the mixture thus made was stirred at 80° C. for 4 hours. After cooling, the hydrochloride of triethylamine thus produced was filtered off and the solvent distilled off.

Crystallization of the residue from methanol gave a product of white powder with melting point of 65° C.

IR (cm$^{-1}$) 2925, 2850: methylene, 1230, 1200: t- butyl, 1100: -O-phenyul 1010: P-O-alkyl, 840: P-O-phenyl H$^1$-NMR (60 MHz, with TMS as standard, in CDCl₃) Delta Value; 0.8: 3H, t, methyl group (stearyl group terminal) 1.2 to 1.3: 73H, sss, tributyl grop and stearyl group 3.2 to 4.4: 4H, dd, methylene group and —O—CH₂— 7.2: 4H, s, aromatic hydrogen Loads of these phosphite compounds to the synthetic resin 100 parts in weight are 0.001 to 10 parts, more preferably 0.01 to 3 parts.

Some examples of typical phenolic antioxidants used in the present invention and represented by the foregoing general formula (II) are enumerated below.

In these compounds R and R' symbolize respectively the following groups.

The loads of these compounds to the synthetic resin, 100 parts in weight are 0.001 to 10 parts by weight, more preferably 0.01 to 3 parts.

The method of adding to the synthetic resin such compounds as represented by the foregoing formulas (I) and (II) is not limmited. A method usually applied may be used as such.

For instance we can use such methods as: dry blending powder or pellet of synthetic resin with powdered additive, spraying additive solution or melt over powder or pellet of synthetic resin or else blending additive dispersion with latex of synthetic resin and then salting-out.

Some examples of the synthetic resins to be stabilized by the present invention are: polyethylene, polypropylene, poly-3-methylbutene and other α-olefin polymers or ethylene-vinyl acetate copolymer, ethylene-propylene copolymer as well as other polyolefins and copolymers thereof; such synthetic resins including halogens as polyvinyl chloride, polyvinyl bromide, polyvinyl fluoride, polyvinylidene chloride, chlorinated polyethylene, chlorinated polypropylene, polyvinylidene fluoride, brominated polyethylene, chlorinated rubber, vinyl chloride-vinyl acetate copolymer vinyl chloride-ethylene copolymer, vinyl chloride-propylene copolymer, vinyl chloride-styrene copolymer, vinyl chlorideisobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride-chlorinated propylene-vinyl acetate terpolymer, vinyl chlorideacrylic ester copolymer, vinyl chloride-maleate ester copolymer, vinyl chloride-metacrylate ester copolymer, vinyl chloride-acrylonitrile copolymer; copolymers of petroleum resin, coumarone resin, polystyrene, polyvinyl acetate, acrylic resin, polyacrilonitrile and styrene with other monomers (for example, maleic anhydride, butadiene, acrylonitrile); ABS resins, so-called heat-resistant ABS resin with part or all of styrene component thereof substituted by α-methylstyrene, so-called high heat-resistant ABS resin in which maleimides are copolymjerized as a component thereof; such methacrylate resins as acrylic ester-butadiene-styrene copolymer, polymethylmethacrylate; and polyvinyl alcohol, polyvinyl formal, polyvinyl butyral, linear polyester, polyphenylene oxide, polyamide, polycarbonate, polyacetal, polyurethane, cellulosic resins, or phenolic resins, urea resins, melamine resins, epoxy resins, unsaturated polyester resins, silicon resins.

Further they may be such rubbers as isoprene rubber, butadiene rubber, acrylonitrile-butadiene copolymer rubber, styrene-butadiene copolymer rubber or blends of these resins.

Adding known phenolic antioxidants to the compositions by this invention will further improve the oxidative stability thereof.

As such phenolic antioxidants we can enumerate: 2,6-dit- butyl-p-cresol, 2,6-diphenyl-4-oxtadecyloxyphenol, distearyl (3,5-di-t-butyl-4-hydroxybenzyl) phosphonate, 4,4'-thiobis(6-t-butyl-m-cresol), 2-octylthio-4,6-di(3',5'-dihydroxyphenoxy)-s-triazine, 2,2'-methylenebis(4-methyl-6-t-butylphenol), 2,2'-methylenebis(4-ethyl-6-t-butylphenol) bis((3,3-bis(4'-hydroxy-3'-t-butylphenyl)butylic acid)glycol ester, 4,4'-butylidenebis(6-t-butyl-m-cresol),2,2'-ethylidenebis(4,6-dit-butylphenol), 2,2'-ethylidenebis(4-sec.-butyl-6-t-butylphenol), 2-t-butyl-4-methyl-6-(2'-acryloyloxine-3'-t-butyl-5'-methylbenzene)phenol, bis((2-t-butyl-4-methyl-6-(2'-hydroxy-3'-t-butyl-5'-methylbenzyl-)phenyl)-)terephtalate, 1,1,3-tris(2'-methyl-4'-hydroxy-5'-t-butylphenyl)butane, 1,3,5-tris(2',6'-dimethyl-3'-hydroxy-4'-t-butylbenzyl)isocyanurate, 1,3,5-tris(3',5'-dit-butyl-4'-hydroxybenzyl)isocyanurate, 1,3,5-tris(3',5'-dit-butyl-4'-hydroxybenzyl)-2,4,6-trimethylbenzene.

Another improvement can be realized by adding sulfuric antioxidants to the composition by the present invention for further oxidative stability. As these sulfuric antioxidants we may enumerate, for instance, such dialkylthiodipropionates as dilauryls, dimyristyls and distearyl esters of thiodiproprionates and β-alkylmercaptopropionic acid esters of such polyols as pentaerythritoltetra(β-dodecylmercaptoproprionate).

The light resistance of the composition by this invention can further be improved by adding thereto such light stabilizers as ultraviolet absorbing agents, hindered amine compounds.

Some examples of these light stabilizers are: 2-hydroxybenzophenones as 2,4-dihydroxybenzophenone, 2-hydroxy-4-methoxybenzophenone, 2-hydroxy-4-octoxybenzophenone, 5,5'-methylenebis(2-hydroxy-4-methoxybenzophenone); such 2-(2'-hydroxyphenyl) benzotriazoles as 2-(2'-hydroxy-5'-methylphenyl) benzotriazole, 2-(2'-hydroxy-5'-t-octylphenyl) benzotriazole, 2-(2'-hydroxy-3',5'-dit-butylphenyl)benzotriazole, 2-(2'-hydroxy-3',5'-dit-butylphenyl)-5-chlorobenzotriazole, 2-(2'-hydroxy-3'-t-butyl5'-methylphenyl)-5chlorobenzotriazole, 2-(2'-hydroxy-3',5'-dicumylphenyl)benzotriazole, 2,2'-methylenebis(4-t-octyl-6-benzotriazoryl) phenol; such benzoates as phenylsalicylate, resorcinol monobenzoate, 2,4-di-t-butylphenyl-3,5'-di-t-butyl-4'-hydroxybenzoate, hexadecyl-3,5-dit-butyl-4-hydroxybenzoate; such substituted oxanhydrides as 2-ethyl2'-ethoxyoxanhydride, 2-ethoxy-4'-dodecyloxanhydride; such cyanoacrylates as ethyl-α-cyano-β,β-diphenylacrylate, methyl-2-cyano-3methyl-3-(p-methoxyphenyl)acrylate; such hindered amine compounds as 2,2,6,6-tetramethyl-4-piperidylstearate, 1,2,2,6,6-pentamethyl-4-piperidylstearate, 2,2,6,-6-tetramethyl-4-piperidylbenzoate, bis(2,2,6,6-tetramethyl-4-piperidyl) sebacate, bis(1,2,2,6,6-pentamethyl-4-piperidyl) sebacate, tetrakis(2,2,6,6-tetramethyl-4-piperidyl)butanetetracarboxylate, tetrakis(1,2,2,6,6-pentamethyl4-piperidyl)1,2,3,4-butanetetracarboxylate, bis(1,2,2,6,6-pentamethyl-4-piperidyl).di(tridecyl-1,2,3,4-butanetetracarboxylate, bis(1,2,2,6,6-pentamethyl-4-piperidyl)-2-butyl-2-(3,5-dit-butyl-4-hydroxybenzyl)malonate, 1-(2-hydroxyethyl)-2,2,6,6-tetramethyl-4-piperidynol/diethyl succinate polycondensate, 1,6-bis(2,2,6,6-tetramethyl-4-piperidylamino)hexane/dibromoethane polycondensate, 1,6-bis(2,2,6,6-tetramethyl-4-piperidylamino-hexane/2,4-dichloro-6-teroctylamino-s-triazine polycondensate, 1,6-bis(2,2,6,6-tetramethyl-4-piperidylamino)hexane/2,4-dichloro-6-morpholinos-triazine polycondensate.

As occasion arises, the compositions by the present invention may contain also: heavy metal inactivation agents, nucleating agents, metallic soap, pigments, filers (loading agents), organic tin compounds, plasticizers epoxides, blowing (foaming) agents, anti-static agents, flameretardants, lubricatns and process aids.

WORKING EXAMPLES

To further illustrate the present invention, and not by way of limitation, the following working examples are given:

Working Example 1

First according to the proportioning as below, pellet was made by extrusion at 280°. Then it underwent injecion molding to be made into test pieces 1 mm in thickness.

With these test pieces we conducted a thermal stability test in an oven at 160° C. To examine their light resistance they were then irradiated by fluorescent lamp for 72 hours and the yellowing factor thereof was measured by Hunder color different meter.

Further to evaluate their processing safety factor, we measured the variation of their melt index with extrusion once effected at 280° C. and then five times repeated (MI(1) and MI(5): g/10 min., 230° C., load: 2160 g), whose results are given in Table 1 hereafter.

| PROPORTIONING | |
|---|---|
| Polypropyrene (Profax 6501) | 100 parts in weight |
| Compound II-8 | 0.1 part in weight |
| Calcium Stearate | 0.05 part in weight |
| Specimen Compound | 0.1 part in weight |

TABLE 1

| NO. | SPECIMEN COMPOUND | THERMAL STABILITY HOURS | YELLOWING FACTOR | MELT INDEX MI(1) | MI(5) | MI(5)/MI(1) |
|---|---|---|---|---|---|---|
| COMPARISON | | | | | | |
| 1-1 | COMP. COMPOUND 1*[1] | 252 | 11.6 | 2.0 | 3.8 | 1.90 |
| 1-2 | COMP. COMPOUND 2*[2] | 264 | 9.8 | 1.9 | 3.5 | 1.84 |
| WORKING | | | | | | |
| 1-1 | COMPOUND I-1 | 324 | 7.4 | 1.7 | 2.3 | 1.35 |
| 1-2 | COMPOUND I-2 | 324 | 7.5 | 1.8 | 2.3 | 1.28 |
| 1-3 | COMPOUND I-3 | 324 | 7.4 | 1.7 | 2.2 | 1.29 |
| 1-4 | COMPOUND I-4 | 336 | 7.4 | 1.8 | 2.3 | 1.28 |
| 1-5 | COMPOUND I-5 | 336 | 7.4 | 1.7 | 2.2 | 1.29 |
| 1-6 | COMPOUND I-6 | 324 | 7.5 | 1.8 | 2.3 | 1.28 |
| 1-7 | COMPOUND I-7 | 312 | 7.6 | 1.8 | 2.5 | 1.39 |
| 1-8 | COMPOUND I-8 | 324 | 7.5 | 1.7 | 2.3 | 1.35 |
| 1-9 | COMPOUND I-9 | 324 | 7.5 | 1.8 | 2.4 | 1.33 |
| 1-10 | COMPOUND I-10 | 336 | 7.4 | 1.7 | 2.3 | 1.35 |

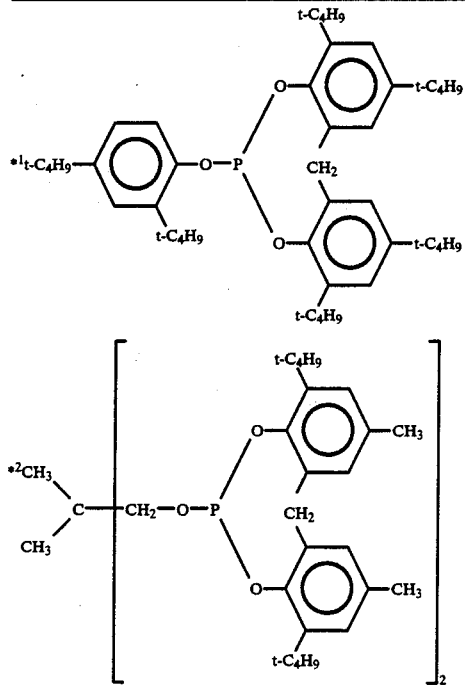

Working Example 2

Using the compounds as below and by a process similar to that in Working Example 1 herebefore, test pieces werre made and processing stability test was conducted in a way similar to in the same example, whose results are shown in Table 2.

| PROPORTIONING | |
|---|---|
| Polypropyrene (Profax 6501) | 100 parts in weight |
| Calcium Stearate | 0.05 part in weight |
| Compound I-5 | 0.1 part in weight |
| Specimen Compound | 0.1 part in weight |

TABLE 2

| No. | SPECIMEN COMPOUND | MI(1)/MI(5) |
|---|---|---|
| Comparison | | |
| 2-1 | 4,4'-n-butylidenebis(2-t-butyl-5-methylphenol) | 2.05 |
| 2-2 | 1,1,3-tris(3-t-butyl-4-hydroxy-5-methylphenyl)butane | 1.82 |
| 2-3 | Ethylenebis((3,3-bis(3-t-butyl-4-hydroxyphenyl)butylate) | 1.86 |
| WORKING | | |
| 2-1 | Compound II-1 | 1.29 |
| 2-2 | Compound II-2 | 1.35 |
| 2-3 | Compound II-3 | 1.35 |
| 2-4 | Compound II-4 | 1.39 |
| 2-5 | Compound II-5 | 1.39 |
| 2-6 | Compound II-6 | 1.28 |
| 2-7 | Compound II-7 | 1.35 |
| 2-8 | Compound II-8 | 1.29 |

Working Example 3

The following compounding ingredients were first extruded at 250°, then injection molded at 250° to be made into test pieces 1 mm thick.

With these test pieces a thermal stability test in an oven at 160° C. was performed, whose results are shown in Table 3.

| PROPORTIONING | |
|---|---|
| Polypropyrene (Profax 6501) | 80 parts in weight |
| Talc | 20 parts in weight |
| Compound II-8 | 0.1 part in weight |
| Calcium Stearate | 0.05 part in weight |
| Diatearylthiodipropionate | 0.2 part in weight |

-continued

| PROPORTIONING | |
|---|---|
| Specimen Compound | 0.1 part in weight |

TABLE 3

| No. | SPECIMEN COMPOUND | THERMAL STABILITY HOURS |
|---|---|---|
| COMPARISON | | |
| 3-1 | Null | 264 |
| 3-2 | Comparison Compound 1 | 336 |
| 3-3 | Comparison Compound 2 | 360 |
| WORKING | | |
| 3-1 | Compound I-1 | 432 |
| 3-2 | Compound I-3 | 408 |
| 3-3 | Compound I-4 | 456 |
| 3-4 | Compound I-5 | 456 |
| 3-5 | Compound I-6 | 432 |
| 3-6 | Compound I-10 | 456 |

Working Example 4

100 parts in weight of unsaturated linear low density polyethylene, 0.02 part in weight of compound II-2 and 0.02 part of specimen compounds were put on a Brabender plastograph and blended for 60 minutes under the condition of 230°x 80 rpm to see variation of the yellowing factor and carbonyl index (CI), whose results are shown in Table 4.

TABLE 4

| No. | SPECIMEN COMPOUND | CI | YELLOWING FACTOR |
|---|---|---|---|
| COMPARISON | | | |
| 4-1 | Null | 2.05 | 50.3 |
| 4-2 | Comparison Compound 1 | 1.95 | 46.5 |
| 4-3 | Comparison Compound 2 | 1.60 | 41.7 |
| WORKING | | | |
| 4-1 | Compound I-2 | 1.25 | 35.2 |
| 4-2 | Compound I-4 | 1.30 | 35.8 |
| 4-3 | Compound I-5 | 1.25 | 34.6 |
| 4-4 | Compound I-6 | 1.30 | 35.5 |
| 4-5 | Compound I-8 | 1.30 | 36.0 |
| 4-6 | Compound I-9 | 1.30 | 35.9 |

Working Example 4

According to the beldning proportioning indicated below, we extruded these ingredients at 240° C. into pellet, which was injection molded thereafter at 280° C. to be made into test pieces of 1 mm in thickness. We then measured their whiteness after reheating for 30 minutes in an oven at 180° C. and the Izod impact strength (kg/cm²) after two weeks' heating in an oven at 120° C. The results are shown in Table 5.

| PROPORTIONING | |
|---|---|
| Unstabilized ABS resin | 100 parts in weight |
| Calcium Stearate | 0.5 part in weight |
| Compound II-2 | 0.2 part in weight |
| Specimen Compound | 0.3 part in weight |

TABLE 5

| No. | SPECIMEN COMPOUND | IZOD IMPACT STRENGTH | WHITENESS |
|---|---|---|---|
| COMPARISON | | | |
| 5-1 | Null | 9.2 | 20.6 |
| 5-2 | Comparison Compound 1 | 11.6 | 23.7 |
| 5-3 | Comparison Compound 2 | 13.8 | 26.5 |
| WORKING | | | |
| 5-1 | Compound I-1 | 16.4 | 32.0 |
| 5-2 | Compound I-2 | 16.4 | 32.0 |
| 5-3 | Compound I-3 | 16.0 | 31.5 |
| 5-4 | Compound I-4 | 16.4 | 31.9 |
| 5-5 | Compound I-5 | 16.6 | 32.4 |
| 5-6 | Compound I-6 | 16.5 | 31.5 |
| 5-7 | Compound I-7 | 15.8 | 31.3 |
| 5-8 | Compound I-8 | 16.4 | 31.8 |
| 5-9 | Compound I-9 | 16.1 | 31.6 |
| 5-10 | Compound I-10 | 16.6 | 32.2 |

Working Example 6

According to the blending proportion as below, the ingredients were extruded at 280° C. to be made into pellet. After holding the pellet at 280° C. for 5 minutes, it was injection molded into test pieces of 12.7 mm in thickness. With these test pieces, we conducted measurement of Izod impact strength and whiteness. The results are shown in Table 6.

| PROPORTIONING | |
|---|---|
| Polycarbonate resin | 50 parts in weight |
| Heat resistant ABS resin ( -methylstyrene content: 40%) | 50 parts in weight |
| Compound II-4 | 0.3 part in weight |
| Specimen Compound | 0.3 part in weight |

TABLE 6

| No. | SPECIMEN COMPOUND | IZOD IMPACT STRENGTH | WHITENESS |
|---|---|---|---|
| COMPARISON | | | |
| 6-1 | Null | | |
| 6-2 | Comparison Compound 1 | 1.0 | 26.3 |
| 6-3 | Comparison Compound 2 | 1.2 | 28.5 |
| EXAMPLE | | | |
| 6-1 | Compound I-2 | 2.0 | 35.0 |
| 6-2 | Compound I-3 | 1.9 | 34.8 |
| 6-3 | Compound I-5 | 2.1 | 35.3 |
| 6-4 | Compound I-6 | 2.1 | 35.2 |
| 6-5 | Compound I-8 | 2.0 | 35.2 |
| 6-6 | Compound I-10 | 2.1 | 35.3 |

Working Example 7

45 parts in weight of polyphenylene oxide resin, 55 parts in weight of shock-resistant polystyrene resin, 0.25 part in weight of compound II-6 and 0.5 part in weight of specimen compound were blended. After extruding at 280° C., they were injection molded at 280° C. to be made into test pieces. With these test pieces we performed measurement of their Izod impact strength after two weeks' reheating at 120° C.

The results of test are shown in Table 7 hereunder.

TABLE 7

| Specimen No. | Compound | IZOD Impact Strength Before Heating | IZOD Impact Strength After Heating |
| --- | --- | --- | --- |
| COMPARISON | | | |
| 7-1 | Comparison Compound 1 | 11.2 | 6.9 |
| 7-2 | Comparison Compound 2 | 11.5 | 7.8 |
| EXAMPLE | | | |
| 7-1 | Compound I-1 | 12.8 | 11.0 |
| 7-2 | Compound I-2 | 12.7 | 10.9 |
| 7-3 | Compound I-4 | 12.7 | 10.8 |
| 7-4 | Compound I-5 | 12.9 | 11.2 |
| 7-5 | Compound I-6 | 12.8 | 11.0 |
| 7-6 | Compound I-8 | 12.5 | 10.7 |
| 7-7 | Compound I-10 | 12.8 | 11.1 |

We claim:

1. A stabilized composition of a synthetic resin which comprises 100 parts by weight of a synthetic resin, 0.001 to 10 parts by weight of a cyclic alkylphosphite compound of 2,2′-alkylidene-bisphenol (I) having the formula (I) and 0.001 to 10 parts by weight of beta-(3,5-dialkyl-4-hydroxyphenyl)-propionic acid ester (II) having the formula (II):

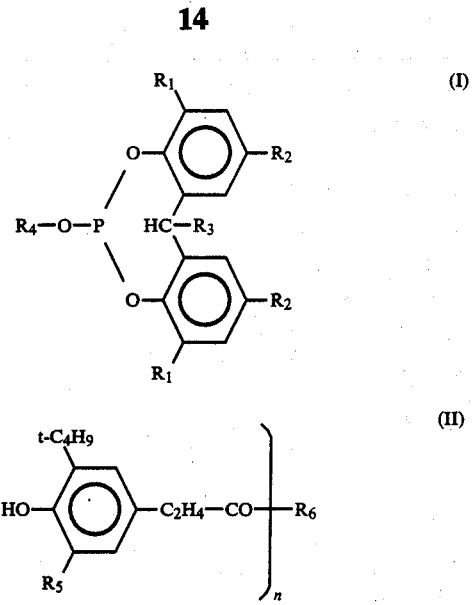

in which $R_1$ is tertiary-butyl or tertiary-amyl, $R_2$ is an alkyl having 1 to 9 carbon atoms, $R_3$ is hydrogen or an alkyl having 1 to 4 carbon atoms, $R_4$ is an alkyl having 1 to 30 carbon atoms, $R_5$ is an alkyl having 1 to 4 carbon atoms, $R_6$ is a residual group of a monohydric alcohol, a dihydric alcohol, a trihydric alcohol or a tetrahydric alcohol and n is a number of 1 to 4.

* * * * *